United States Patent
Fukunaga

(10) Patent No.: US 10,335,019 B2
(45) Date of Patent: Jul. 2, 2019

(54) IMAGE PICKUP ELEMENT AND ENDOSCOPE DEVICE

(71) Applicant: OLYMPUS CORPORATION, Hachioji-shi, Tokyo (JP)

(72) Inventor: Yasuhiro Fukunaga, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 88 days.

(21) Appl. No.: 15/450,520

(22) Filed: Mar. 6, 2017

(65) Prior Publication Data

US 2017/0172393 A1  Jun. 22, 2017

Related U.S. Application Data

(63) Continuation of application No. PCT/JP2015/075487, filed on Sep. 8, 2015.

(30) Foreign Application Priority Data

Sep. 9, 2014  (JP) ................. 2014-183211

(51) Int. Cl.
*A61B 1/04* (2006.01)
*H04N 9/07* (2006.01)
(Continued)

(52) U.S. Cl.
CPC .............. *A61B 1/043* (2013.01); *A61B 1/042* (2013.01); *G02B 23/2423* (2013.01);
(Continued)

(58) Field of Classification Search
CPC ........ H04N 9/07; H04N 5/2256; H04N 5/332; H04N 2005/2255; A61B 1/043;
(Continued)

(56) References Cited

U.S. PATENT DOCUMENTS

2003/0209651 A1  11/2003  Iwasaki
2004/0124791 A1*  7/2004  Takahashi .............. A61B 1/045
                                                      315/297
(Continued)

FOREIGN PATENT DOCUMENTS

CN     101677109 A    3/2010
JP     2003-332551 A  11/2003
(Continued)

OTHER PUBLICATIONS

International Search Report dated Nov. 10, 2015, issued in counterpart application No. PCT/JP2015/075487, w/ English translation. (4 pages).
(Continued)

*Primary Examiner* — Tung T Vo
(74) *Attorney, Agent, or Firm* — Westerman, Hattori, Daniels & Adrian, LLP

(57) ABSTRACT

An image pickup element includes a first substrate, a second substrate, first pixels, and second pixels irradiated with light transmitted through the first pixels, and the second pixel includes a first PN junction surface parallel to a light-receiving surface, and a second PN junction surface positioned deeper than the first PN junction surface and parallel to the light-receiving surface, and the second pixel generates a second signal corresponding to light of a second wavelength band from electric charge obtained by the second PN junction surface.

10 Claims, 15 Drawing Sheets

(51) Int. Cl.
*G02B 23/24* (2006.01)
*H01L 27/146* (2006.01)
*H04N 5/225* (2006.01)
*H04N 5/33* (2006.01)

(52) U.S. Cl.
CPC ..... *G02B 23/2453* (2013.01); *G02B 23/2484* (2013.01); *H01L 27/14621* (2013.01); *H01L 27/14634* (2013.01); *H01L 27/14645* (2013.01); *H01L 27/14647* (2013.01); *H01L 27/14649* (2013.01); *H04N 5/2256* (2013.01); *H04N 5/332* (2013.01); *H04N 9/07* (2013.01); *H04N 2005/2255* (2013.01)

(58) Field of Classification Search
CPC .............. A61B 1/042; H01L 27/14649; H01L 27/14645; H01L 27/14634; H01L 27/14647; H01L 27/14621; G02B 23/2484; G02B 23/2423; G02B 23/2453
USPC .......................................................... 348/65
See application file for complete search history.

(56) References Cited

U.S. PATENT DOCUMENTS

| | | | |
|---|---|---|---|
| 2008/0079807 A1* | 4/2008 | Inuiya | A61B 1/042 348/70 |
| 2010/0067002 A1 | 3/2010 | Ishii | |
| 2012/0257030 A1* | 10/2012 | Lim | A61B 1/00009 348/70 |
| 2013/0075607 A1* | 3/2013 | Bikumandla | H01L 27/14632 250/332 |
| 2014/0009662 A1* | 1/2014 | Toda | H04N 9/045 348/336 |
| 2014/0194748 A1 | 7/2014 | Yamamoto et al. | |
| 2015/0171146 A1 | 6/2015 | Ooki et al. | |
| 2015/0204492 A1* | 7/2015 | Bichler | C09K 11/0883 362/84 |

FOREIGN PATENT DOCUMENTS

| | | |
|---|---|---|
| JP | 2007-053731 A | 3/2007 |
| JP | 3962122 B2 | 8/2007 |
| JP | 2010-68925 A | 4/2010 |
| JP | 2010-073824 A | 4/2010 |
| JP | 2013-70030 A | 4/2013 |
| JP | 2014-135535 A | 7/2014 |

OTHER PUBLICATIONS

Office Action dated Jun. 8, 2018, issued in counterpart Chinese Application No. 201580047380.7, with English translation, (23 pages).

Office Action dated Nov. 20, 2018, issued in counterpart Japanese application No. 2014-183211, with English translation. (5 pages).

* cited by examiner

IMAGE PICKUP ELEMENT AND ENDOSCOPE DEVICE

CROSS REFERENCE TO RELATED APPLICATIONS

This application is a continuation application based on a PCT Patent Application No. PCT/JP2015/075487, filed on Sep. 8, 2015, whose priority is claimed on Japanese Patent Application No. 2014-183211, filed Sep. 9, 2014. The content of both the PCT Application and the Japanese Application are incorporated herein by reference.

BACKGROUND OF THE INVENTION

Field of the Invention

The present invention relates to an image pickup element and an endoscope device.

Description of the Related Art

In recent years, in fields of medical applications such as endoscopes, fluorescence agents which can be administered to the human body for observing lesions such as cancer or blood flow have been applied. The most common fluorescence agent which can be administered to the human body is a fluorescence agent called indocyanine green (ICG), which excites and emits fluorescence in an infrared wavelength region.

A technique capable of capturing a normal visible image and an infrared image with a fluorescence wavelength of ICG at the same time is known (for example, refer to Japanese Patent Publication No. 3962122). FIG. 14 is a block diagram which shows a configuration of a conventionally known fluorescence endoscope device capable of capturing a normal visible image and an infrared image with a fluorescence wavelength of ICG at the same time. In the example shown in FIG. 14, a fluorescence endoscope device 1A causes visible light to be incident on RGB image pickup elements 26, 27, and 28 using a dichroic mirror 22. As a result, the RGB image pickup elements 26, 27, and 28 generate image signals. An infrared light component is reflected by the dichroic mirror 22, passes through an excitation light cut filter 23, and is incident on an infrared image pickup element 25. Accordingly, the infrared image pickup element 25 generates an ICG fluorescence image signal.

FIG. 15 is a graph which shows characteristics of a band-pass filter 12 disposed in a light source device 3A of the conventionally known fluorescence endoscope device 1A. A line 1501 is a line which shows transmittance of the band-pass filter 12. With these characteristics, the band-pass filter 12 transmits a visible component of light of a xenon light source 11 and an excitation wavelength component of an ICG fluorescence substance and emits the components toward a subject.

FIG. 16 is a graph which shows characteristics of the dichroic mirror 22 of the conventionally known fluorescence endoscope device 1A. A line 1601 is a line which shows transmittance of the dichroic mirror 22. With these characteristics, the dichroic mirror 22 is configured to transmit a visible component and reflect an infrared component.

FIG. 17 is a graph which shows characteristics of the excitation light cut filter 23 of the conventionally known fluorescence endoscope device 1A. A line 1701 is a line which shows transmittance of the excitation light cut filter 23. With these characteristics, the excitation light cut filter 23 is configured to transmit only components with a wavelength longer than a fluorescence wavelength of the ICG fluorescence substance so that the infrared image pickup element 25 can image only a fluorescence image.

FIG. 18 is a graph which shows characteristics of the excitation wavelength and the fluorescence wavelength of the conventionally known ICG fluorescence substance. A line 1801 is a line which shows intensity of excitation light. A line 1802 is a line which shows intensity of fluorescence. In order to generate an ICG fluorescence image signal, it is necessary to remove the excitation wavelength component emitted toward a subject by a light source and to image light with only a fluorescence wavelength component using an image pickup element.

With the above configuration, the fluorescence endoscope device 1A can image a visible image and a fluorescence image at the same time by separating visible light and infrared light using the dichroic mirror 22 and causing them to pass through the excitation cut filter 23. The fluorescence endoscope device 1A is a system which can perform image pickup by emitting light with a visible component from the light source device 3A and light with an excitation light component from a laser light source 7 to a subject.

In addition, a technology related to a hybrid PD-PD imager is known (for example, refer to U.S. Patent Application, Publication No. 2013/0075607). FIG. 19 is a cross-sectional view which shows a conventionally known image pickup element of a hybrid structure in which two layers of the image pickup element are stacked and image pickup is performed in the lower layer using light that has passed through the upper layer. In an example shown in FIG. 19, a first substrate 221 and a second substrate 222 are stacked. First photodiodes 223-1 to 223-$n$ are formed on the first substrate 221 of the upper layer. Second photodiodes 224-1 to 224-$n$ are formed on the second substrate 222 of the lower layer.

With this configuration, light transmitted through the first photodiodes 223-1 to 223-$n$ formed on the first substrate 221 of the upper layer can be received by the second photodiodes 224-1 to 224-$n$ formed on the second substrate 222 of the lower layer. Accordingly, it is possible to perform image capturing at the first photodiodes 223-1 to 223-$n$ formed on the first substrate 221 and the second photodiodes 224-1 to 224-$n$ formed on the second substrate 222 at the same time.

Light incident on silicon, which is a material widely used as a CCD or CMOS image pickup element, is absorbed at a deeper point when it has a longer wavelength. Accordingly, if the first substrate is set as a thin image sensor like a BSI using a hybrid PD-PD imager as shown in FIG. 19, a component with a long wavelength like the ICG fluorescence wavelength described in a graph of FIG. 18 can pass through the first substrate 221 and can be imaged in the second substrate 222. In this case, compared to the configuration described in FIG. 14, a dichroic mirror is not necessary and a camera head can be decreased in size.

SUMMARY OF THE INVENTION

According to a first aspect of the present invention, an image pickup element includes: a first substrate; a second substrate which is stacked on the first substrate; first pixels which are disposed in a matrix form on the first substrate, each of the first pixels having a first light-receiving element, the first pixel being irradiated with incident light of a first wavelength band including a visible band and incident light of a second wavelength band having a longer wavelength than the first wavelength band and including a near infrared region, the first pixel generating a first signal corresponding to light of the first wavelength band; and second pixels which are disposed in a matrix form on the second substrate and irradiated with light transmitted through the first pixels, wherein the second pixel has a first PN junction surface parallel to a light-receiving surface and a second PN junction surface positioned deeper than the first PN junction surface and parallel to the light-receiving surface, a P-type layer and an N-type layer of the first PN junction surface are connected at a same potential, and the second pixel generates a second signal corresponding to light of the second wavelength band from electric charge obtained by the second PN junction surface.

According to a second aspect of the present invention, an image pickup element comprising: a first substrate second substrate which is stacked on the first substrate; first pixels which are disposed in a matrix form on the first substrate, each of the first pixels having a first light-receiving element, the first pixel being irradiated with incident light of a first wavelength band including a visible band and incident light of a second wavelength band having a longer wavelength than the first wavelength band and including a near infrared region, the first pixel generating a first signal corresponding to light of the first wavelength band; and second pixels which are disposed in a matrix form on the second substrate and irradiated with light transmitted through the first pixels, wherein the first pixel has a first PN junction surface parallel to a light-receiving surface and a second PN junction surface positioned deeper than the first PN junction surface and parallel to the light-receiving surface, a P-type layer and an N-type layer of the first PN junction are connected at a same potential, and the first pixel generates a second signal corresponding to light of the second wavelength band from electric charge obtained by the second PN junction surface.

According to a third aspect of the present invention, in the first aspect or the second aspect, the first PN junction surface may generate electric charge with light having a wavelength included in the first wavelength band.

According to a fourth aspect of the present invention, in any one of the first to third aspects, the first signal may be corrected using a third signal generated by the first PN junction surface.

According to a fifth aspect of the present invention, in any one of the first to fourth aspects, an amount of light incident on the first pixel and the second pixel may be controlled using the third signal.

According to a sixth aspect of the present invention, an image pickup element includes: a first substrate; a second substrate which is stacked on the first substrate; first pixels which are disposed in a matrix form on the first substrate, each of the first pixels having a first light-receiving element, the first pixel being irradiated with incident light of a first wavelength band including a visible band and incident light of a second wavelength band having a longer wavelength than the first wavelength band and including a near infrared region, the first pixel generating a first signal corresponding to light of the first wavelength band; and second pixels which are disposed in a matrix form on the second substrate and irradiated with light transmitted through the first pixels, wherein the second pixel has a first PN junction surface parallel to a light-receiving surface and a second PN junction surface positioned deeper than the first PN junction surface and parallel to the light-receiving surface, a P-type layer and an N-type layer of the first PN junction surface are connected at a same potential, and the second pixel generates a second signal corresponding to light of the second wavelength band from electric charge obtained by the second PN junction surface, and the first pixel has a third PN junction surface parallel to a light-receiving surface and a fourth PN junction surface positioned deeper than the third PN junction surface and parallel to the light-receiving surface, a P-type layer and an N-type layer of the third PN junction surface are connected at a same potential, and the first pixel generates a fourth signal corresponding to light of the second wavelength band from electric charge obtained by the fourth PN junction surface.

According to a seventh aspect of the present invention, an endoscope device which administers a fluorescence substance made of indocyanine green derivative-labeled antibodies to an object to be inspected and performs diagnosis using an endoscope, the endoscope device including the image pickup element according to any one of the first to sixth aspects, wherein an optical filter which transmits light of a visible band and a near infrared fluorescence wavelength band of a fluorescence substance and does not transmit an excitation wavelength band component near a fluorescence wavelength band is disposed on a light-receiving surface side of the first pixel, and the first wavelength band includes a visible band and the second wavelength band includes a fluorescence band of the fluorescence substance.

According to an eighth aspect of the present invention, in the seventh aspect, a first image of a visible band may be created from the first signal, a second image of a fluorescence wavelength band may be created from the second signal, and the first substrate, the second substrate, and the optical filter may be disposed at a tip of the endoscope.

DETAILED DESCRIPTION OF THE EMBODIMENTS

First Embodiment

Figure 1:
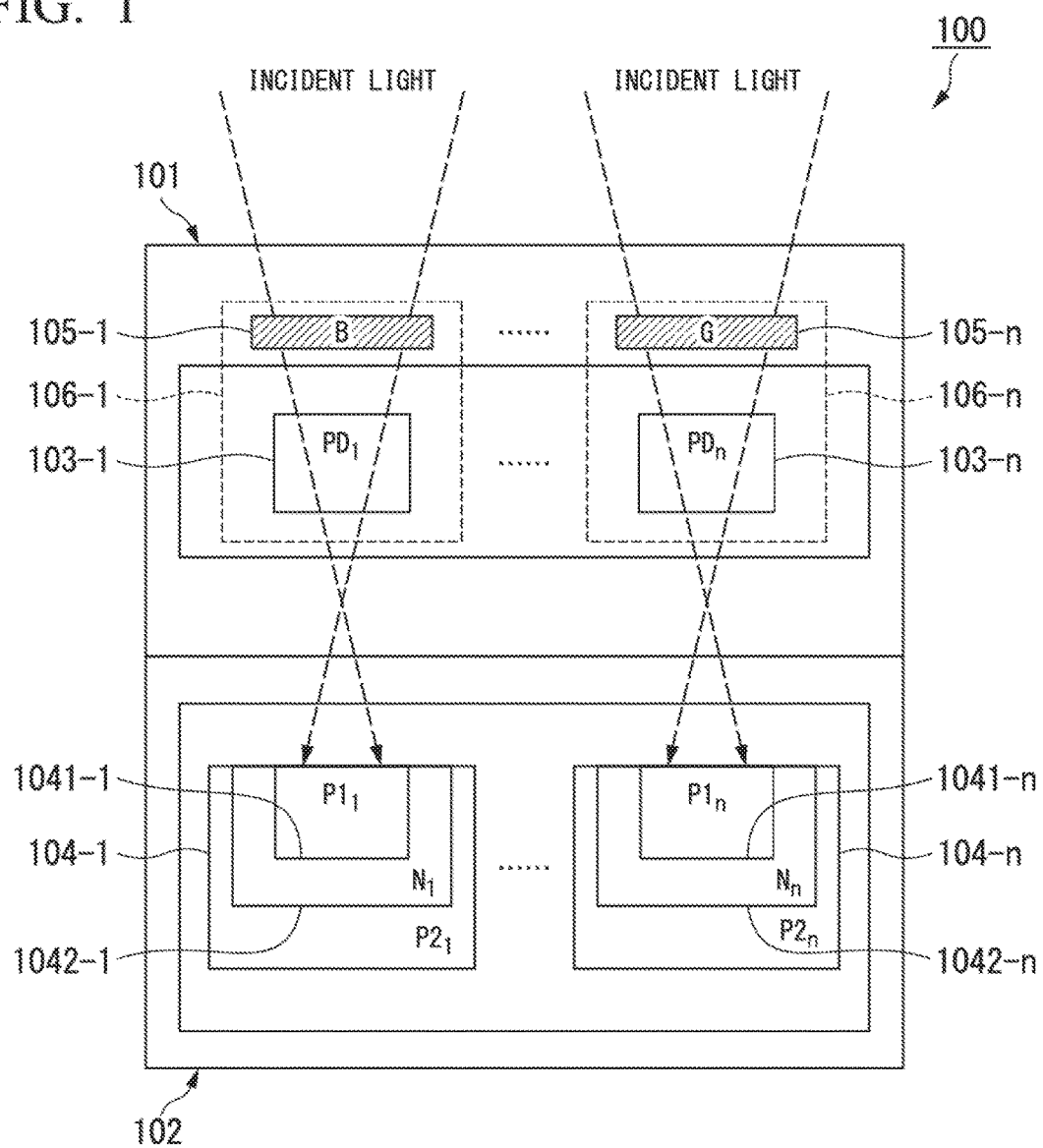
FIG. 1 is a cross-sectional view which shows a cross section of an image pickup element according to a first embodiment of the present invention.

Hereinafter, a first embodiment of the present invention will be described with reference to the drawings. First, a configuration of an image pickup element 100 will be described. FIG. 1 is a cross-sectional view which shows a cross section of the image pickup element 100 according to the embodiment. In the illustrated example, the image pickup element 100 includes a first substrate 101, a second substrate 102, first photodiodes 103-1 to 103-n (first light-receiving elements), second pixels 104-1 to 104-n (second photodiodes, second light-receiving elements), and color filters 105-1 to 105-n. In addition, a surface on a side irradiated with incident light is defined as a light-receiving surface.

The first substrate 101 and the second substrate 102 are stacked. The first substrate 101 and the second substrate 102 are silicon substrates. In addition, the first substrate 101 transmits some of incident light.

The first photodiodes 103-1 to 103-n are disposed in the first substrate 101. The color filters 105-1 to 105-n are one of a filter (R) which transmits red light, a filter (G) which transmits green light, and a filter (B) which transmits blue light, and are disposed on a light-receiving surface side of the first photodiodes 103-1 to 103-n. That is, on-chip RGB color filters 105-1 to 105-n are disposed on the first photodiodes 103-1 to 103-n. The disposition of the color filters 105-1 to 105-n will be described below.

The color filters 105-1 to 105-n transmit light with an infrared wavelength regardless of whether the color filters are the filter (R) which transmits red light, the filter (G) which transmits green light, or the filter (B) which transmits blue light. Moreover, generally in an image pickup element and the like tier a digital camera, an IR cut filter (infrared light cut filter) is provided on a light-receiving surface side, but the IR cut filter is not used in this embodiment.

In the embodiment, sets of each of the first photodiodes 103-1 to 103-n and each of the color filters 105-1 to 105-n are set as first pixels 106-1 to 106-n. For example, a set of a first photodiode 103-1 and a color filter 105-1 is set as a first pixel 106-1. The first photodiodes 103-1 to 103-n output a first signal corresponding to an exposure amount.

The second pixels 104-1 to 104-n are disposed in the second substrate 102. The second pixels 104-1 to 104-n include p-type layers P11 to P1n, n-type layers N1 to Nn, and p-type layers P21 to P2n, respectively, and include first PN junction surfaces 1041-1 to 1041-n parallel to a light-receiving surface, and second PN junction surfaces 1042-1 to 1042-n which are positioned deeper than the first PN junction surfaces 1041-1 to 1041-n and parallel to the light-receiving surface. With this configuration, the second pixels 104-1 to 104-n generate a second signal from electric charges obtained by the second PN junction surfaces 1042-1 to 1042-n. In addition, the second pixels 104-1 to 104-n generate a third signal from electric charges obtained by the first PN junction surfaces 1041-1 to 1041-n.

Figure 2:
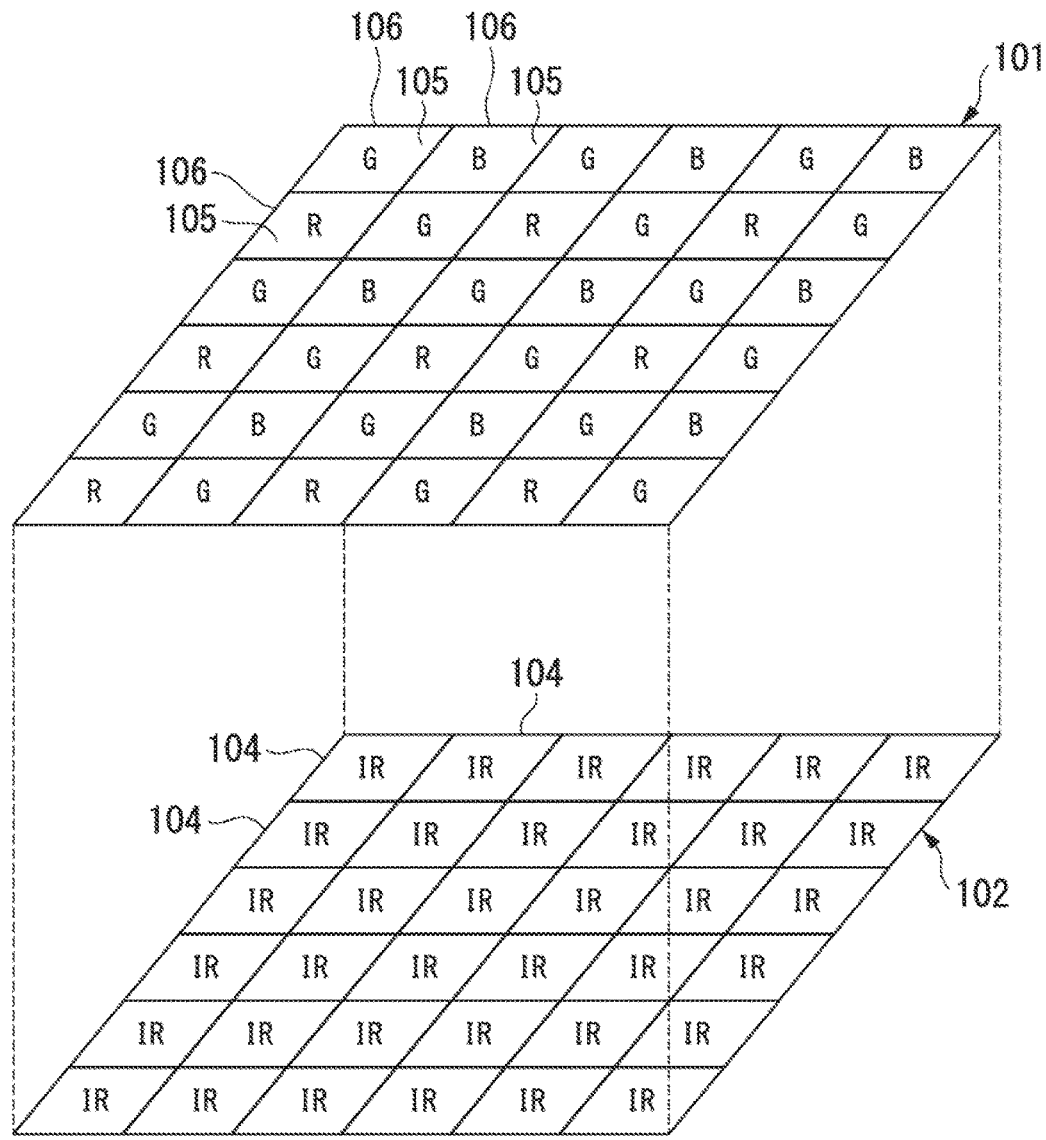
FIG. 2 is a schematic diagram which shows an arrangement of color filters according to the first embodiment of the present invention.

Next, an arrangement of the color filters 105 will be described. FIG. 2 is a schematic diagram which shows the arrangement of the color filters 105 according to the embodiment. In the example shown in FIG. 2, the first substrate 101 includes a total of 36 first pixels 106 which are regularly arranged in a two-dimensional from of 6 rows and 6 columns. In addition, the second substrate 102 includes a total of 36 second pixels 104 which are regularly arranged in a two-dimensional form of 6 rows and 6 columns. As shown in FIG. 2, the color filters 105 (the color filters R, the color filters G, and the color filters B) are arranged in a Bayer arrangement in the first substrate 101.

The first pixel 106 is irradiated with incident light of a first wavelength band including a visible band and a second wavelength band having a longer wavelength than the first wavelength band and including a near infrared region, and generates a first signal corresponding to light of the first wavelength hand.

The second pixel 104 is irradiated with light transmitted through the first pixel 106, for example, light including infrared light. With such a pixel disposition, it is possible to image a visible image on the first substrate 101 and an infrared image on the second substrate 102 at the same time.

The number of first pixels 106 included in the first substrate 101 and second pixels 104 included in the second substrate 102 is not limited to the example shown in FIG. 2, and may be any number. In addition, the arrangement of the first pixels 106 and the second pixels 104 may be any arrangement.

Moreover, in the example shown in FIG. 2, the second pixels 104 are disposed under the first pixels 106 to correspond to each other, but are not limited thereto. It is also possible to set a pixel size of the second pixels 104 to be an integer multiple of that of the first pixels 106.

Figure 3:
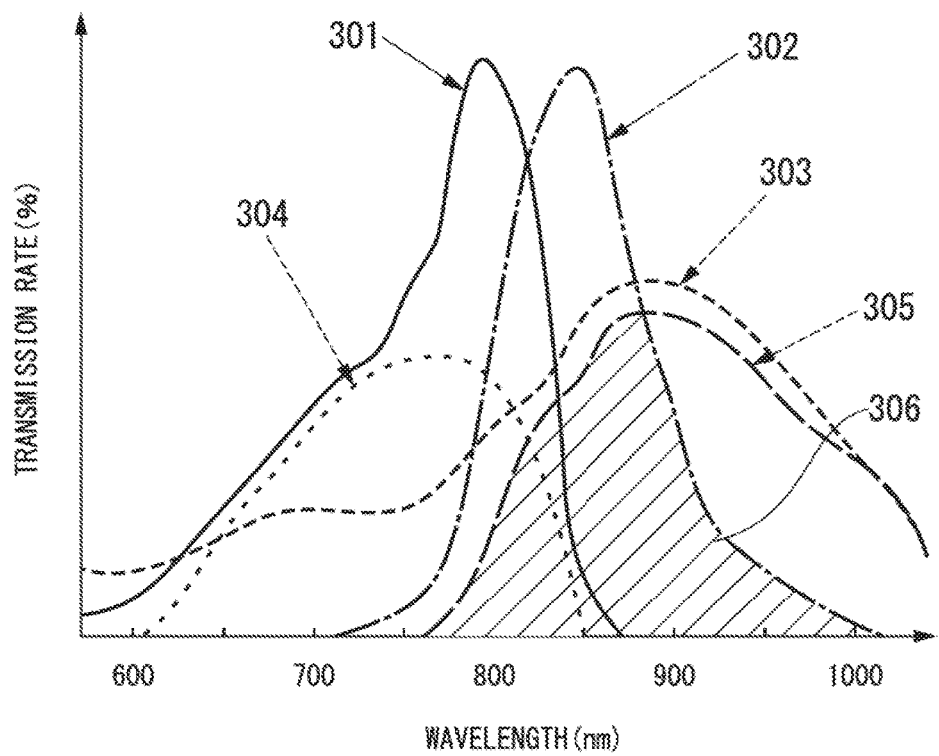
FIG. 3 is a graph which shows characteristics of excitation light, fluorescence, light transmitted through a first substrate, light detected by a first PN junction surface, and light detected by a second PN junction surface according to the first embodiment of the present invention.

FIG. 3 is a graph which shows characteristics of excitation light, fluorescence, light transmitted through the first substrate 101, light detected by the first PN junction surfaces 1041-1 to 1041-n, and light detected by the second PN junction surfaces 1042-1 to 1042-n. A horizontal axis of the graph shows a wavelength (nm). A vertical axis of the graph shows a transmission rate (%). A line 301 is a line showing characteristics of the excitation light. A line 302 is a line showing characteristics of the fluorescence. A line 303 is a line showing characteristics of the light transmitted through the first substrate 101. A line 304 is a line showing characteristics of the light detected by the first PN junction surfaces 1041-1 to 1041-*n*. A line 305 is a line showing characteristics of the light detected by the second PN junction surfaces 1042-1 to 1042-*n*.

In the embodiment, the second pixels 104 disposed in the second substrate 102 include the first PN junction surfaces 1041-1 to 1041-*n* and the second PN junction surfaces 1042-1 to 1042-*n* positioned deeper than the first PN junction surfaces 1041-1 to 1041-*n*. With this configuration, the second PN junction surfaces 1042-1 to 1042-*n* can detect light transmitted through the first substrate 101 and the first PN junction surfaces 1041-1 to 1041-*n* (light of a region 306 in FIG. 3).

Accordingly, the second PN junction surfaces 1042-1 to 1042-*n* can detect a fluorescence component excluding more excitation light component than an unnecessary excitation light component (light with wavelengths of 600 to 800 nm) on the first substrate 101 or the first PN junction surfaces 1041-1 to 1041-*n* in a shallow side layer, and can generate a second signal corresponding to light of the second wavelength band. Therefore, the image pickup element 100 can remove an excitation light component emitted toward the fluorescence substance or a visible component, and can acquire images with a wavelength (fluorescence wavelength (860 nm)) of interest with high S/N.

Figure 4:
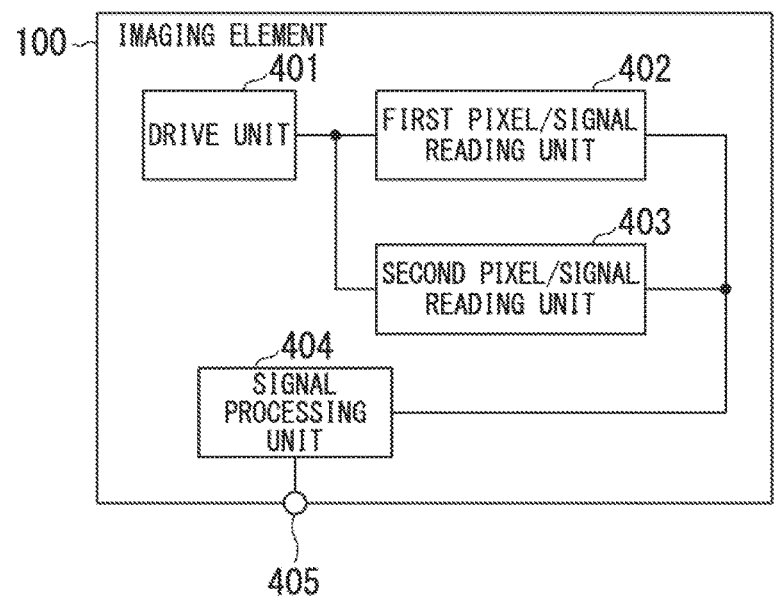
FIG. 4 is a block diagram which shows a configuration of an image pickup element according to the first embodiment of the present invention.

Next, a configuration of the image pickup element 100 will be described. FIG. 4 is a block diagram which shows the configuration of the image pickup element 100 according to the embodiment. The image pickup element 100 includes a drive unit 401, a first pixel/signal reading unit 402, a second pixel/signal reading unit 403, a signal processing unit 404, and a signal output terminal 405. The drive unit 401 transmits a control signal and drives the first pixel/signal reading unit 402 and the second pixel/signal reading unit 403. The first pixel/signal reading unit 402 includes the first pixels 106-1 to 106-*n*, reads a first signal generated by the first pixels 106-1 to 106-*n*, and outputs the first signal to the signal processing unit 404. The second pixel/signal reading unit 403 includes the second pixels 104-1 to 104-*n*, reads a second signal generated by the second pixels 104-1 to 104-*n*, and outputs the second signal to the signal processing unit 404.

The signal processing unit 404 generates a first image on the basis of the first signal input from the first pixel/signal reading unit 402. The first signal is an R signal corresponding to an intensity of red light, a G signal corresponding to an intensity of green light, and a B signal corresponding to an intensity of blue light. That is, the first signal is an RGB signal. Therefore, the first image generated by the signal processing unit 404 is an RGB image.

In addition, the signal processing unit 404 generates a second image on the basis of the second signal input from the second pixel/signal reading unit 403. The second signal is a fluorescence signal corresponding to an intensity of light centered on 830 nm. Therefore, the second image generated by the signal processing unit 404 is a fluorescence image. Moreover, the signal processing unit 404 outputs the generated first and second images from the signal output terminal 405. The signal processing unit 404 may perform image processing such as noise reduction or overlap between the RGB image and the fluorescence image.

Figure 5:
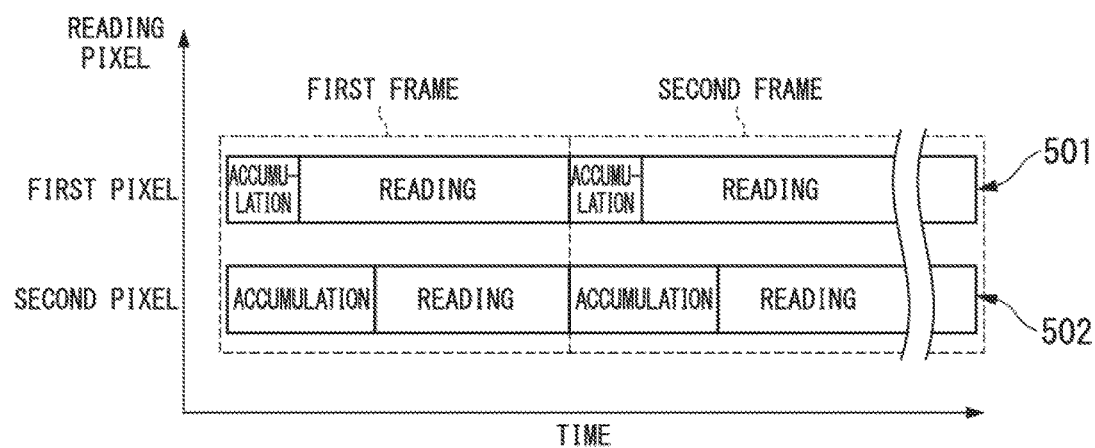
FIG. 5 is a timing chart which shows a drive timing of an image pickup element according to the first embodiment of the present invention.

Next, a driving method of the image pickup element 100 will be described. FIG. 5 is a timing chart which shows a driving timing of the image pickup element 100 in the embodiment. In the illustrated example, a timing chart 501 which shows a driving timing of the first pixel 106 and a timing chart 502 which shows a driving timing of the second pixel 104 are shown. A horizontal axis of the timing chart is time.

Since the second pixel 104 is irradiated only with light transmitted through the first pixel 106, an amount of light radiated to the second pixel 104 is less than an amount of light radiated to the first pixel 106. Therefore, as shown in FIG. 5, an electric charge accumulation time (exposure time) of the first pixel 106 is longer than an electric charge accumulation time (exposure time) of the second pixel 104 in the embodiment. In the embodiment, a reading time, which is a time to read a signal from each pixel, is set so that the RGB image and the fluorescence image have the same frame rate.

As described above, according to the embodiment, the first substrate 101 and the second substrate 102 are stacked. In addition, the second substrate 102 is disposed at a position overlapping the first substrate 101 and on a side opposite to the light-receiving surface side of the first substrate 101 when viewed from the light-receiving surface side of the first substrate 101. In addition, the first substrate 101 transmits light. Moreover, the second substrate 102 is irradiated with the light transmitted through the first substrate 101.

Accordingly, the first pixel 106 of the first substrate 101 and the second pixel 104 of the second substrate 102 can be exposed to light at the same time. That is, generation of the first signal by the first pixel 106 and generation of the second signal by the second pixel 104 can be performed at the same time. Accordingly, the signal processing unit 404 can generate the first image (RGB image) based on the first signal and the second image (fluorescence image) based on the second signal at the same time.

In addition, according to the embodiment, the second pixels 104 disposed in the second substrate 102 include the first PN junction surfaces 1041-1 to 1041-*n*, and the second PN junction surfaces 1042-1 to 1042-*n* positioned deeper than the first PN junction surfaces 1041-1 to 1041-*n*. With this configuration, the second PN junction surfaces 1042-1 to 1042-*n* can detect light transmitted through the first substrate 101 and the first PN junction surfaces 1041-1 to 1041-*n*.

As a result, the second PN junction surfaces 1042-1 to 1042-*n* can detect a fluorescence component excluding more than an unnecessary light component on the first substrate 101 and the first PN junction surfaces 1041-1 to 1041-*n* in a shallow side layer and generate a second signal corresponding to light of the second wavelength band. Accordingly, the image pickup element 100 can remove the excitation light component emitted toward the fluorescence substance or the visible component, and can image a fluorescence image corresponding to a wavelength of interest with high accuracy.

Second Embodiment

Next, a second embodiment of the present invention will be described. The image pickup element 100 of the first embodiment is different from an image pickup element of the embodiment in a configuration of the first photodiode included in the first substrate. The other configurations are the same as in the first embodiment.

Figure 6:
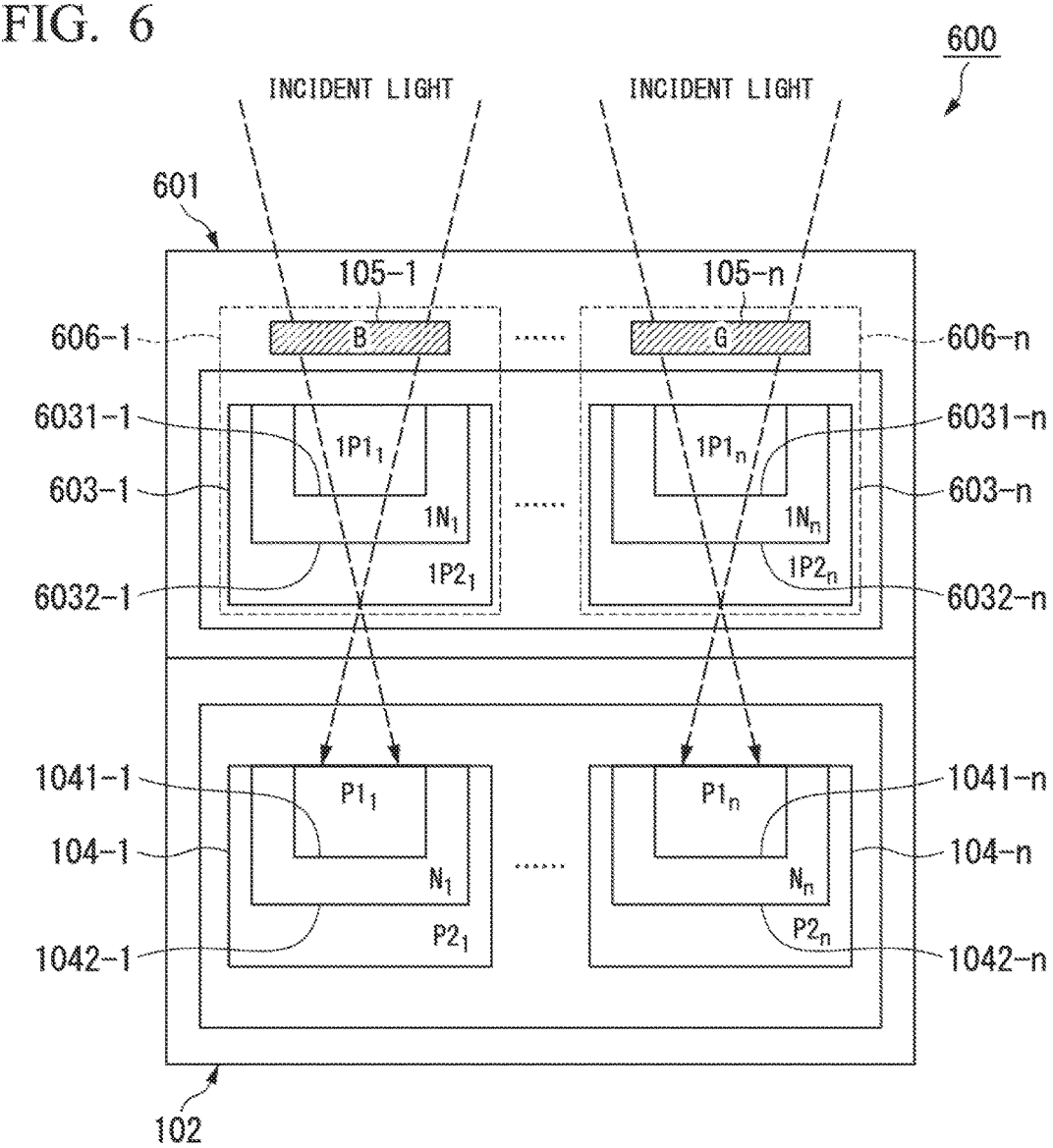
FIG. 6 is a cross-sectional view which shows a cross section of an image pickup element according to a second embodiment of the present invention.

FIG. 6 is a cross-sectional view which shows a cross section of an image pickup element 600 according to the embodiment. In the illustrated example, the image pickup element 600 includes a first substrate 601, a second substrate 102, first photodiodes 603-1 to 603-*n* (first light-receiving elements), second pixels 104-1 to 104-*n* (second photodiodes, second light-receiving elements), and color filters 105-1 to 105-*n*. In addition, a surface of a side irradiated with incident light is defined as a light-receiving surface.

The first substrate 601 and the second substrate 102 are stacked. The first substrate 601 and the second substrate 102 are silicon substrates. Moreover, the first substrate 601 transmits some of incident light.

The first photodiodes 603-1 to 603-*n* are disposed in the first substrate 601. In addition, the first photodiodes 603-1 to 603-*n* include p-type layers 1P11 to 1P1*n*, n-type layers 1N1 to 1N*n*, and p-type layers 1P21 to 1P2*n*, respectively, and include first PN junction surfaces 6031-1 to 6031-*n* which are parallel to the light-receiving surface, and second PN junction surfaces 6032-1 to 6032-*n* which are positioned deeper than the first PN junction surfaces 6031-1 to 6031-*n* and parallel to the light-receiving surface. With this configuration, the first photodiodes 603-1 to 603-*n* generate a second signal from electric charges obtained by the second PN junction surfaces 6032-1 to 6032-*n*. In addition, the first photodiodes 603-1 to 603-*n* generate a first signal from electric charges obtained by the first PN junction surfaces 6031-1 to 6031-*n*.

The color filters 105-1 to 105-*n* are one of filters (R) which transmit red light, filters (G) which transmit green light, and filters (B) which transmit blue light, and are disposed on the light-receiving surface side of the first photodiodes 603-1 to 603-*n*. That is, the on-chip RGB color filters 105-1 to 105-*n* are disposed on the first photodiodes 603-1 to 603-*n*. Disposition of the color filters 105-1 to 105-*n* is the same as in the first embodiment.

In the embodiment, sets of each of the first photodiodes 603-1 to 603-*n* and each of the color filters 105-1 to 105-*n* are set as the first pixels 606-1 to 606-*n*. For example, a set of the first photodiode 603-1 and the color filter 105-1 is set as a first pixel 606-1.

The second pixels 104-1 to 104-*n* are disposed in the second substrate 102. In addition, the second pixels 104-1 to 104-*n* include p-type layers P11 to P1*n*, n-type layers N1 to N*n*, and p-type layers P21 to P2*n*, respectively, and include first PN junction surfaces 1041-1 to 1041-*n* which are parallel to the light-receiving surface, and second PN junction surfaces 1042-1 to 1042-*n* which are positioned deeper than the first PN junction surfaces 1041-1 to 1041-*n* and parallel to the light-receiving surface. With this configuration, the second pixels 104-1 to 104-*n* generate a second signal from electric charges obtained by the second PN junction surfaces 1042-1 to 1042-*n*. In addition, the second pixels 104-1 to 104-*n* generate a third signal from electric charges obtained by the first PN junction surfaces 1041-1 to 1041-*n*.

Figure 7:
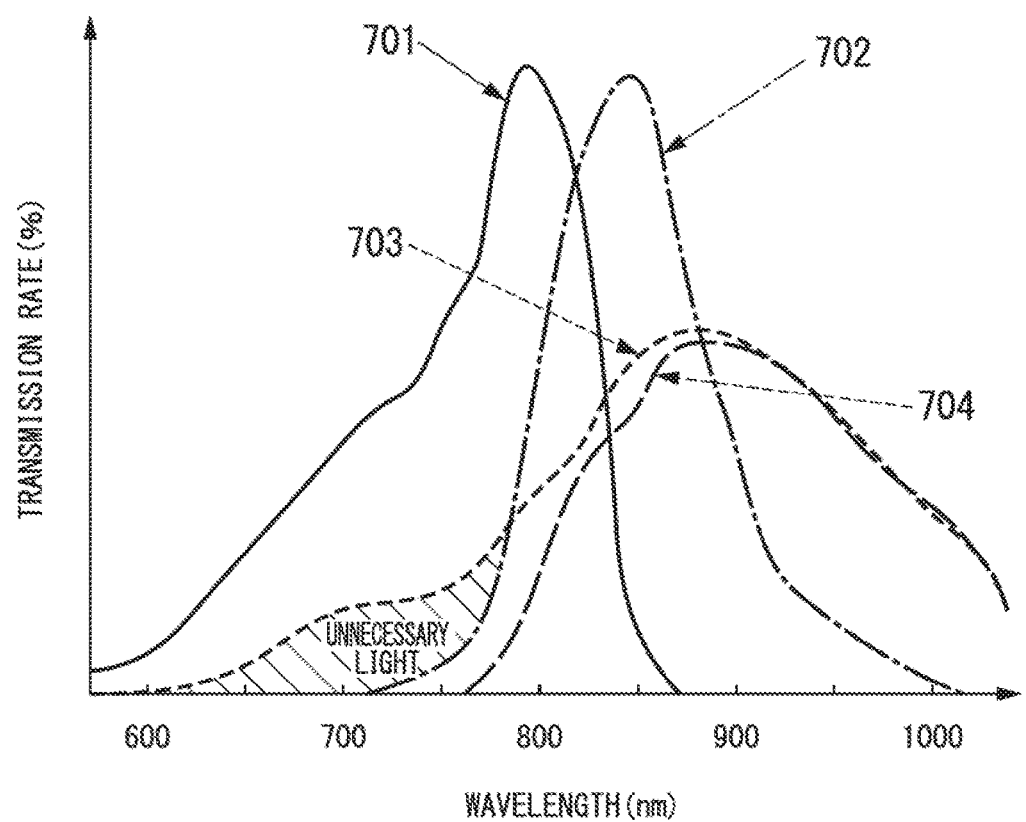
FIG. 7 is a graph which shows characteristics of excitation light, fluorescence, light transmitted through a first substrate, and light detected by second PN junction surface.

FIG. 7 is a graph which shows characteristics of excitation light, fluorescence, light transmitted through the first substrate 101, and light detected by the second PN junction surfaces 1042-1 to 1042-*n*. A horizontal axis of the graph shows a wavelength (nm). A vertical axis of the graph shows a transmission rate (%). A line 701 is a line showing characteristics of the excitation light. A line 702 is a line showing characteristics of the fluorescence. A line 703 is a line showing characteristics of the light transmitted through the first substrate 601. A line 704 is a line showing characteristics of the light detected by the second PN junction surfaces 1042-1 to 1042-*n*.

In the embodiment, the first photodiodes 603-1 to 603-*n* include the p-type layers 1P11 to 1P1*n*, the n-type layers 1N1 to 1N*n*, and the p-type layers 1P21 to 1P2*n*, respectively, and include the first PN junction surfaces 6031-1 to 6031-*n* which are parallel to the light-receiving surface, and second PN junction surfaces 6032-1 to 6032-*n* which are positioned deeper than the first PN junction surfaces 6031-1 to 6031-*n* and parallel to the light-receiving surface. With this configuration, an excitation light component transmitted through the first substrate 601 is less than in the first embodiment (refer to the line 303 in FIG. 3).

Accordingly, the second PN junction surfaces 1042-1 to 1042-*n* can detect a fluorescence component excluding an unnecessary light component on the first substrate 601 or the first PN junction surfaces 1041-1 to 1041-*n* in a shallow side layer and generate a second signal corresponding to light of the second wavelength band. Accordingly, the image pickup element 600 can remove the excitation light component emitted toward the fluorescence substance or the visible component, and can image a fluorescence image corresponding to a wavelength of interest with high accuracy.

Third Embodiment

Next, a third embodiment of the present invention will be described. The image pickup element 100 in the first embodiment is different from an image pickup element in the embodiment in that a p-type layer and an n-type layer on a first PN junction surface included in a second pixel are electrically connected to each other to have the same potential. The other configurations are the same as in the first embodiment.

Figure 8:
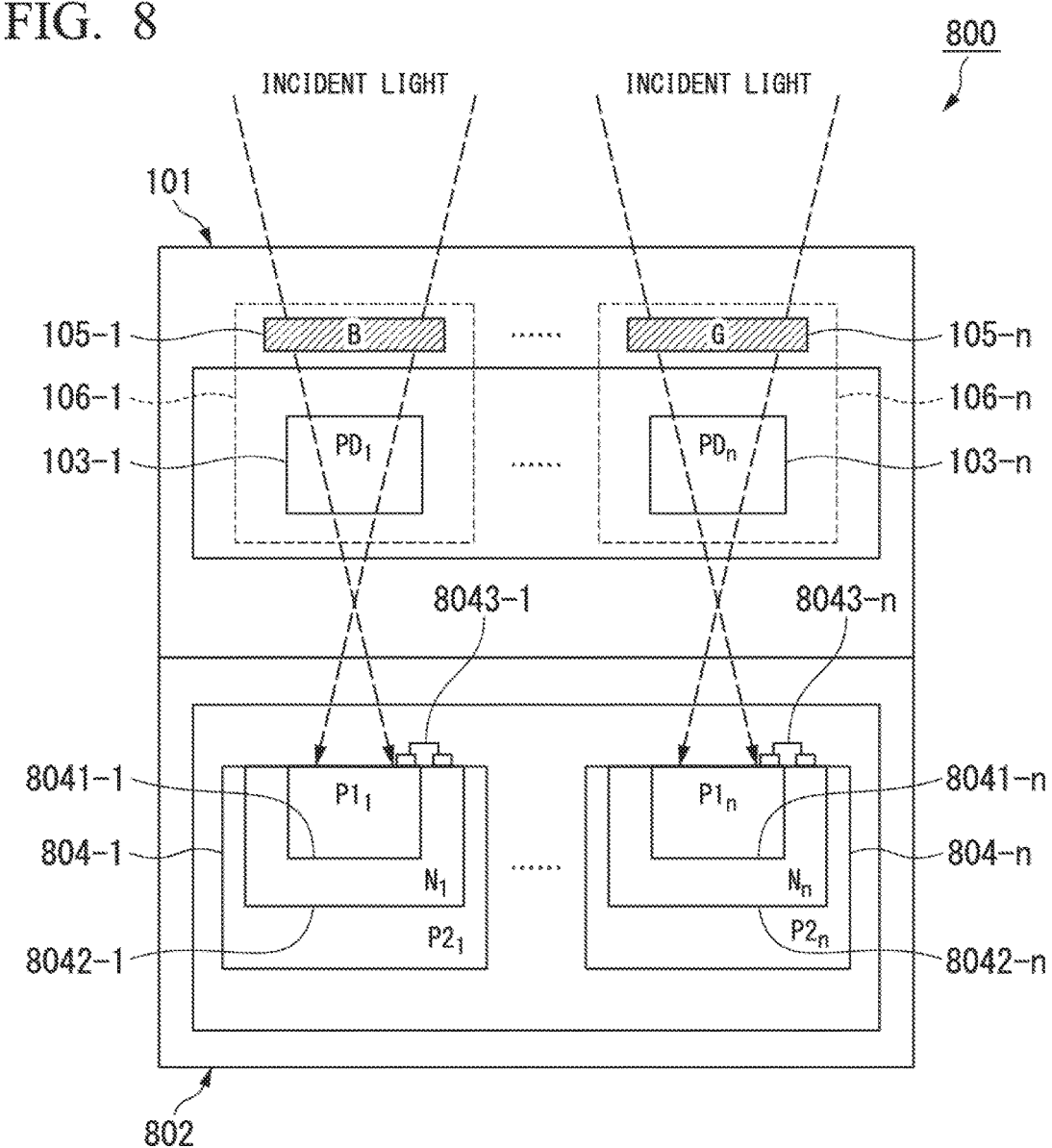
FIG. 8 is a cross-sectional view which shows a cross section of an image pickup element according to a third embodiment of the present invention.

FIG. 8 is a cross-sectional view which shows a cross section of an image pickup element 800 according to the embodiment. As shown in FIG. 8, the image pickup element 800 includes a first substrate 101, a second substrate 802, first photodiodes 103-1 to 103-*n* (first light-receiving elements), second pixels 804-1 to 804-*n* (second photodiodes, second light-receiving elements), and color filters 105-1 to 105-*n*. In addition, a surface on a side irradiated with incident light is defined as a light-receiving surface.

The first substrate 101 and the second substrate 802 are stacked. The first substrate 101 and the second substrate 802 are silicon substrates. In addition, the first substrate 101 transmits some of incident light.

The first photodiodes 103-1 to 103-*n* are disposed in the first substrate 101. The color filters 105-1 to 105-*n* are one of filters (R) which transmit red light, filters (G) which transmit green light, and filters (B) which transmit blue light, and are disposed on a light-receiving surface side of the first photodiodes 103-1 to 103-*n*. That is, on-chip RGB color filters 105-1 to 105-*n* are disposed on the first photodiodes 103-1 to 103-*n*. Disposition of the color filters 105-1 to 105-*n* is the same as in the first embodiment.

In the embodiment, sets of each of the first photodiodes 103-1 to 103-*n* and each of the color filters 105-1 to 105-*n* are set as first pixels 106-1 to 106-*n*. For example, a set of the first photodiode 103-1 and the color filter 105-1 is set as a first pixel 106-1. The first photodiodes 103-1 to 103-*n* output a first signal corresponding to an exposure amount.

The second pixels 804-1 to 804-*n* are disposed in the second substrate 802. In addition, the second pixels 804-1 to 804-*n* include p-type layers P11 to P1*n*, n-type layers N1 to N*n*, and p-type layers P21 to P2*n*, respectively, and include first PN junction surfaces 8041-1 to 8041-*n* which are parallel to the light-receiving surface, and second PN junction surfaces 8042-1 to 8042-*n* which are positioned deeper than the first PN junction surfaces 8041-1 to 8041-*n* and parallel to the light-receiving surface. In addition, the p-type layers P11 to P1*n* and the n-type layers N1 to N*n* of the first PN junction surface 8041 are electrically connected using connection units 8043-1 to 8043-*n*, respectively, to have the same potential. Accordingly, it is possible to suppress occurrence of electric charges by the first PN junction surface 8041. As a result, it is possible to improve accuracy in the second signal generated by the second PN junction surfaces 8042-1 to 8042-*n*.

Fourth Embodiment

Next, a fourth embodiment of the present invention will be described. The image pickup element 100 of the first embodiment is different from an image pickup element of the embodiment in that the RGB image based on the first signal generated by the first pixels 106-1 to 106-*n* of the first substrate 101 is corrected using a third signal generated by the first PN junction surfaces 1041-1 to 1041-*n* and a signal generated by the second PN junction surfaces 1042-1 to 1042-*n*. The other configurations are the same as in the first embodiment.

Figure 9:
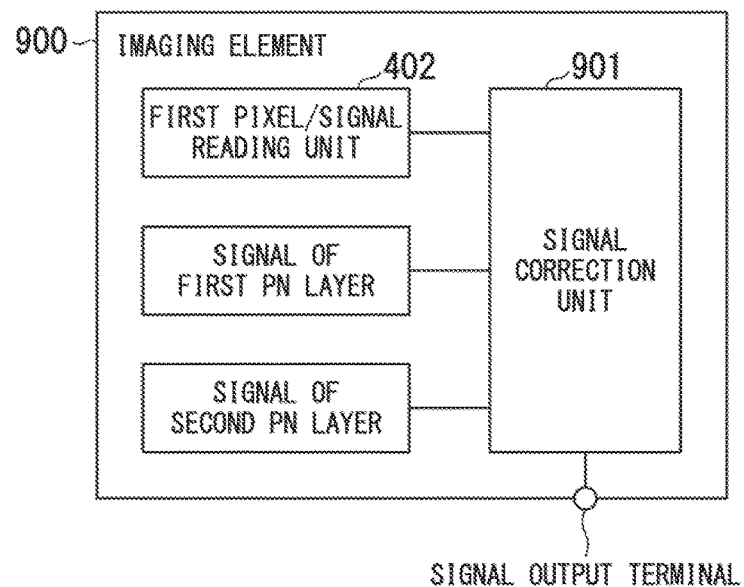
FIG. 9 is a block diagram which shows a configuration of an image pickup element according to a fourth embodiment of the present invention.

FIG. 9 is a block diagram which shows a configuration of an image pickup element 900 according to the embodiment. The image pickup element 900 includes a first pixel signal reading unit 402 and a signal correction unit 901. The first signal generated by the first pixels 106-1 to 106-*n* contains an infrared component in addition to a visible component (RGB component). In addition, the third signal generated by the first PN junction surfaces 1041-1 to 1041-*n* and the signal generated by the second PN junction surfaces 1042-1 to 1042-*n* are signals corresponding to the infrared component contained in the first signal. Therefore, the signal correction unit 901 performs a difference process on the infrared components from the first signal, thereby generating images with only the visible component. Accordingly, it is possible to further improve an image quality of a first image (RGB image, visible image).

Fifth Embodiment

Next, a fifth embodiment of the present invention will be described. The embodiment is different from the first embodiment in that the embodiment includes an ICG filter on a light-receiving surface side of an image pickup element. The other configurations are the same as in the first embodiment.

Figure 10:
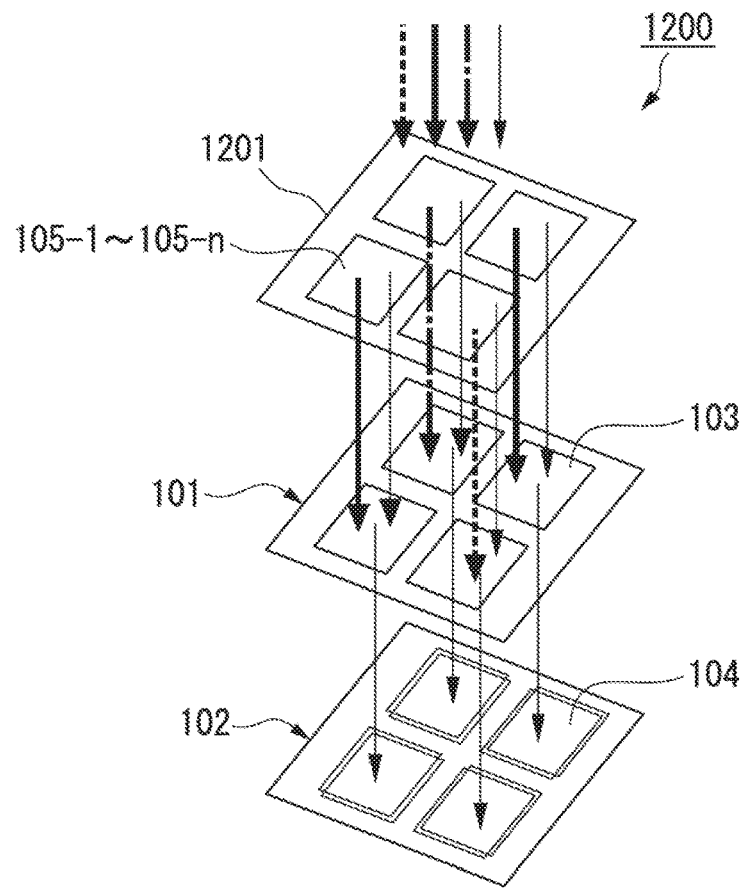
FIG. 10 is a schematic diagram which shows a configuration of an image pickup element according to a fifth embodiment of the present invention.

FIG. 10 is a schematic diagram which shows a configuration of an image pickup element 1200 according to the embodiment. The image pickup element 1200 shown in FIG. 10 includes a first substrate 101, a second substrate 102, a plurality of first photodiodes 103 (first light-receiving elements), a plurality of second pixels 104 (second photodiodes, second light-receiving elements), a plurality of color filters 105, and an ICG filter 1201.

Configurations of the first substrate 101, the second substrate 102, the first photodiode 103, the second pixel 104, and the color filter 105 are the same as in the first embodiment. The ICG filter 1201 is disposed on a light-receiving surface side of the color filter 105. The ICG filter 1201 is an optical filter which cuts excitation light of ICG and transmits only light with a fluorescence wavelength.

Figure 11:
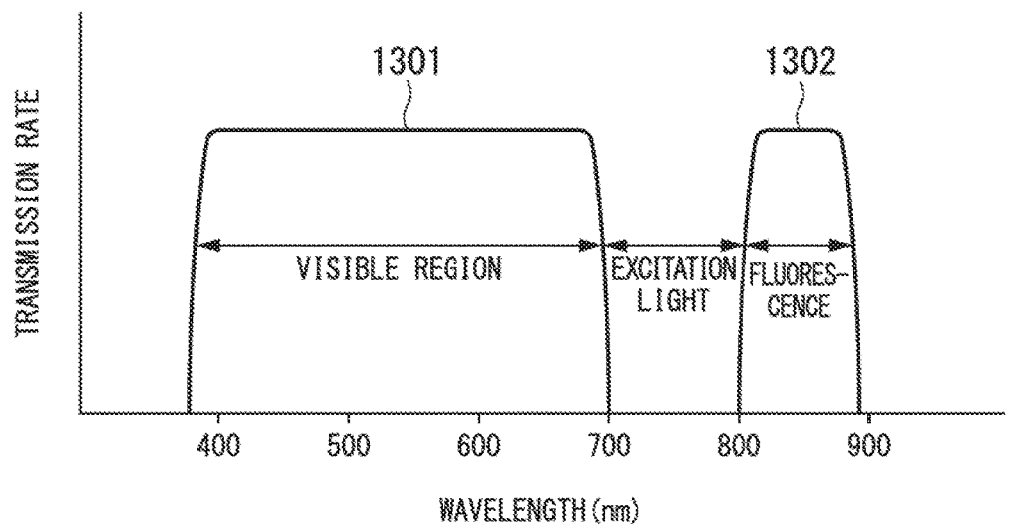
FIG. 11 is a graph which shows spectral characteristics of an ICG filter according to a fifth embodiment of the present invention.

FIG. 11 is a graph which shows spectral characteristics of the ICG filter 1201 according to the embodiment. A horizontal axis of the graph shows a wavelength (nm). A vertical axis of the graph shows transmittance of a visible region of the ICG filter 1201. A line 1301 shows transmittance of the visible region of the ICG filter 1201. A line 1302 shows transmittance of fluorescence of the ICG filter 1201. As shown in FIG. 11, the ICG filter 1201 transmits light of a visible region and fluorescence and does not transmit excitation light. In an example shown in FIG. 11 the ICU filter 1201 which attenuates a fluorescence portion at 900 nm is shown, but the ICG filter may be a high-pass type which transmits everything over 800 nm.

As a result, the second PN junction surfaces 1042-1 to 1042-*n* can generate a second signal corresponding to light of a second wavelength band by detecting a fluorescence component excluding unnecessary light components at the ICG filter 1201, the first substrate 101, and the first PN junction surfaces 1041-1 to 1041-*n* in a shallow side layer. Accordingly, the image pickup element 1200 can remove an excitation light component emitted toward a fluorescence substance or a visible component, and can image a fluorescence image corresponding to a wavelength of interest with high accuracy.

Sixth Embodiment

Next, a sixth embodiment of the present invention will be described. In the embodiment, an endoscope device equipped with any one of image pickup elements described in the first embodiment to the fifth embodiment will be described.

Figure 12:
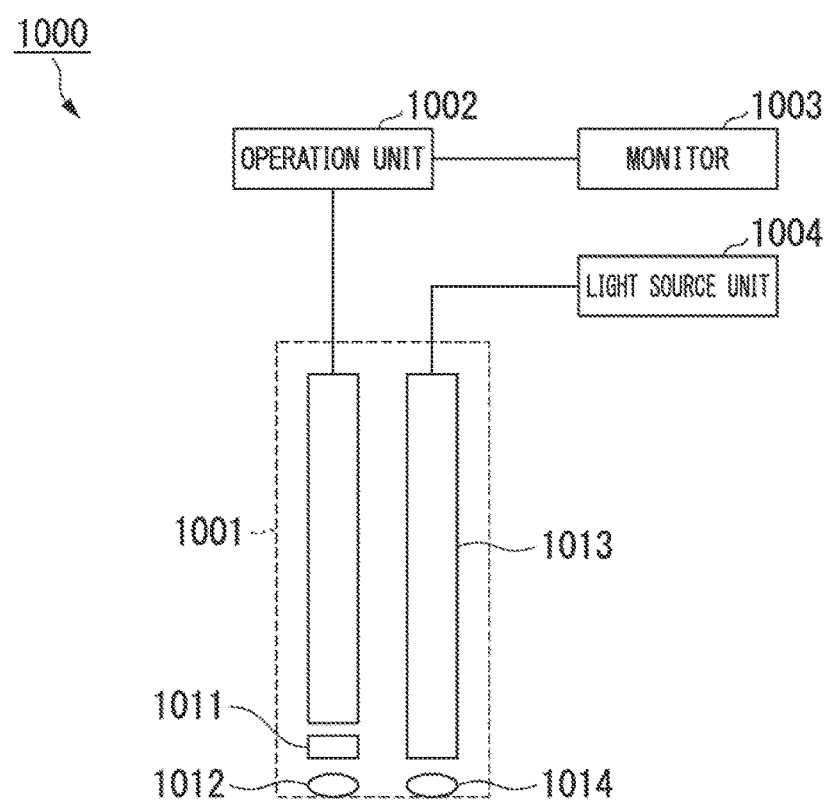
FIG. 12 is a block diagram which shows a configuration of an endoscope device according to a sixth embodiment of the present invention.

FIG. 12 is a block diagram which shows a configuration of an endoscope device according to the embodiment. In the illustrated example, an endoscope device 1000 includes an endoscope scope 1001, an operation unit 1002, a monitor 1003, and a light source unit 1004. The operation unit 1002 performs controls on each unit of the endoscope device 1000. The monitor 1003 is, for example, a liquid crystal display and displays images. The light source unit 1004 is, for example, an LED, and emits light.

The endoscope scope 1001 includes an image pickup element 1011, an image pickup lens 1012, a light guide 1013, and a lighting lens 1014. The image pickup element 1011 is one of the image pickup elements described in the first embodiment to the fifth embodiment. The image pickup element 1011 is disposed at a tip of the endoscope scope 1001. In addition, the image pickup lens 1012 is disposed on a light-receiving surface side of the image pickup element 1011. Moreover, the lighting lens 1014 is disposed at a tip of the endoscope scope 1001.

The light guide 1013 irradiates the lighting lens 1014 with light emitted by the light source unit 1004. The lighting lens 1014 collects light emitted from the light guide 1013 and irradiates a subject with the light. The image pickup lens 1012 collects light from the subject and irradiates the image pickup element 1011 with the light. The image pickup element 1011 generates a first image and a second image on the basis of the light emitted by the image pickup lens 1012. The operation unit 1002 causes the first image and the second image generated by the image pickup element 1011 to be displayed on a monitor 1003.

For example, the image pickup elements described in the first embodiment to the fifth embodiment can be decreased in size and can image highly accurate RGB images and fluorescence images at the same time. Therefore, it is possible to image highly accurate RGB images and fluorescence images at the same time by using one of the image pickup elements described in the first embodiment to the fifth embodiment in the endoscope device 1000. For example, highly accurate RGB images and fluorescence images can be used for cancer diagnosis and ICG observation during a surgical operation.

Seventh Embodiment

Next, a seventh embodiment of the present invention will be described. The embodiment is different from the sixth embodiment in that an amount of light (an excitation light component) of the light source unit 1004 is adjusted using a third signal generated by the first PN junction surfaces 1041-1 to 1041-n. The other configurations are the same as in the sixth embodiment.

Figure 13:
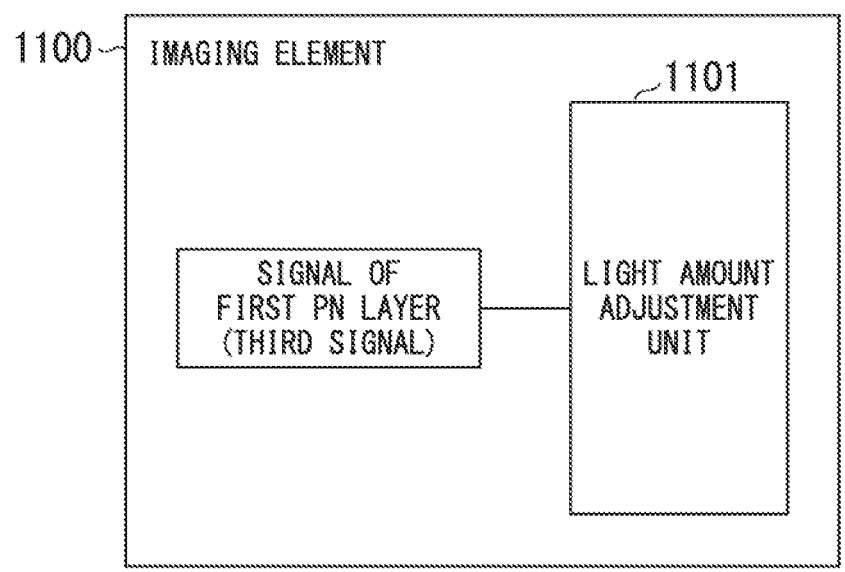
FIG. 13 is a block diagram which shows a configuration of an image pickup element according to a seventh embodiment of the present invention.
Figure 14:
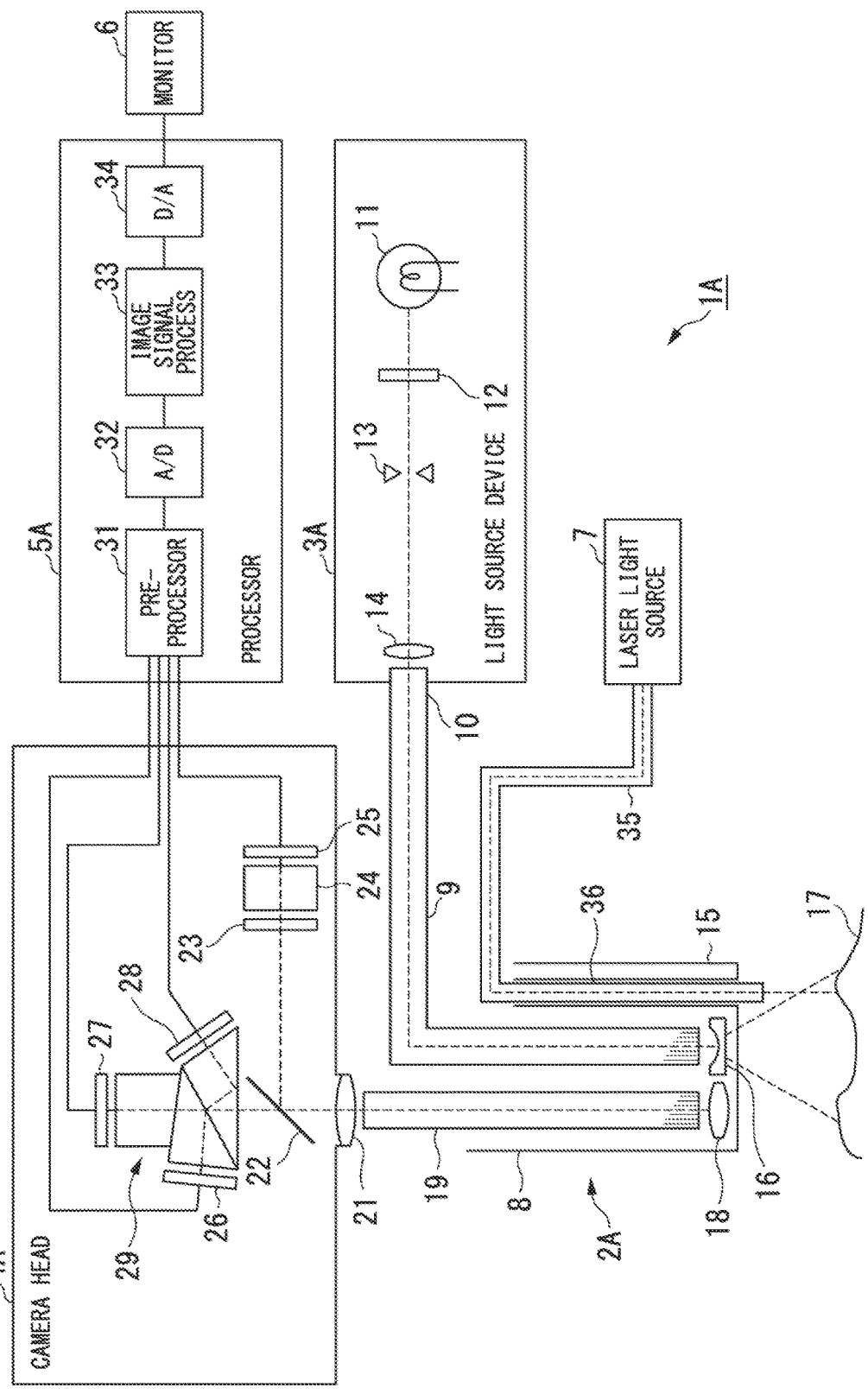
FIG. 14 is a block diagram which shows a configuration of a conventionally known fluorescence endoscope device capable of capturing a normal visible image and an infrared image with an ICG fluorescence wavelength at the same time.
Figure 15:
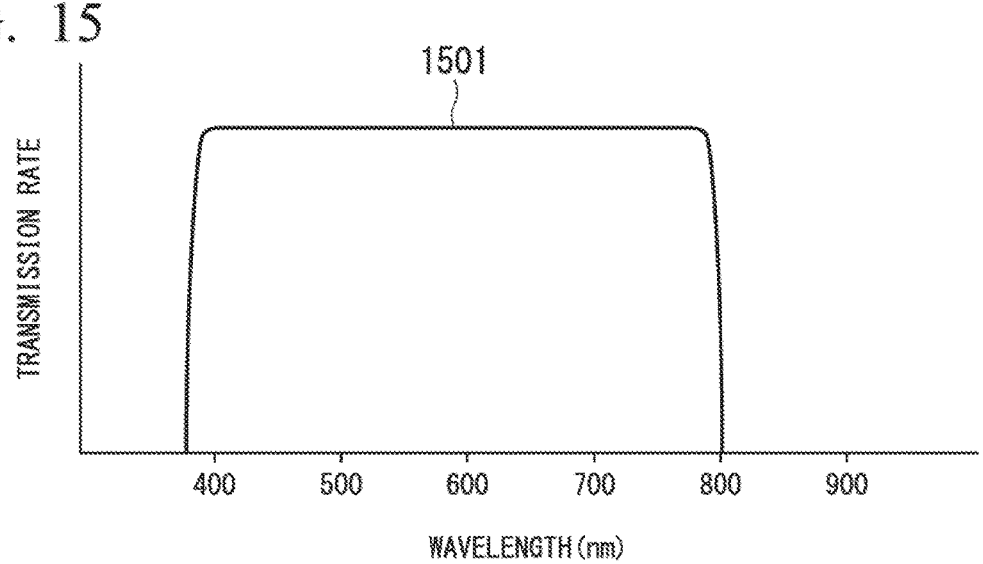
FIG. 15 is a graph which shows characteristics of a band-pass filter disposed in a light source device of the conventionally known fluorescence endoscope device.
Figure 16:
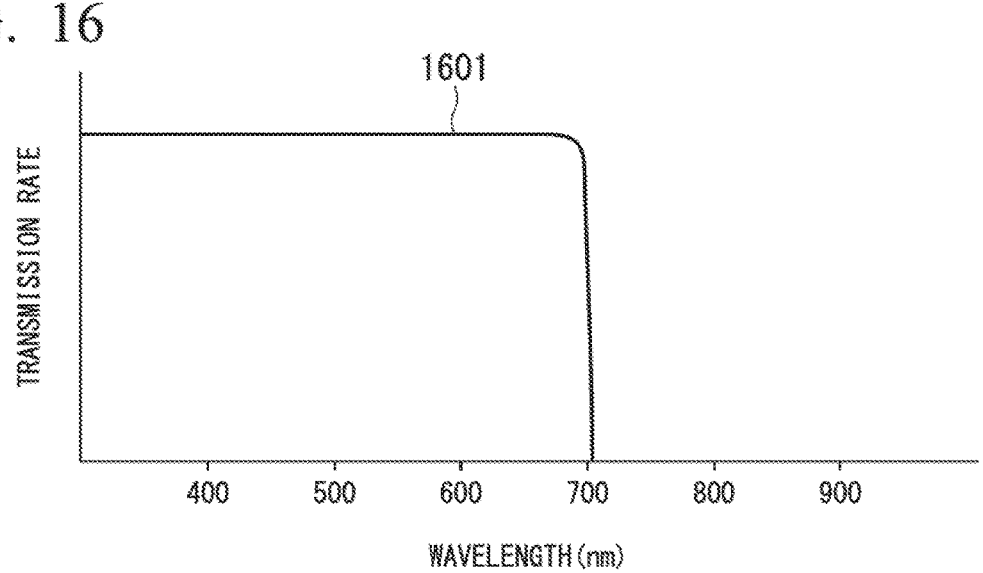
FIG. 16 is a graph which shows characteristics of a dichroic mirror of the conventionally known fluorescence endoscope device.
Figure 17:
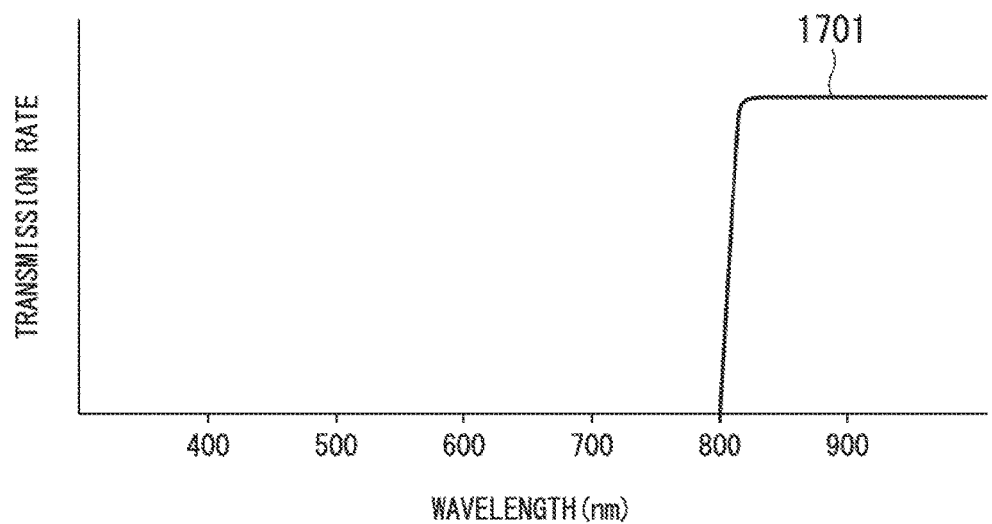
FIG. 17 is a graph which shows characteristics of an excitation light cut filter of the conventionally known fluorescence endoscope device.
Figure 18:
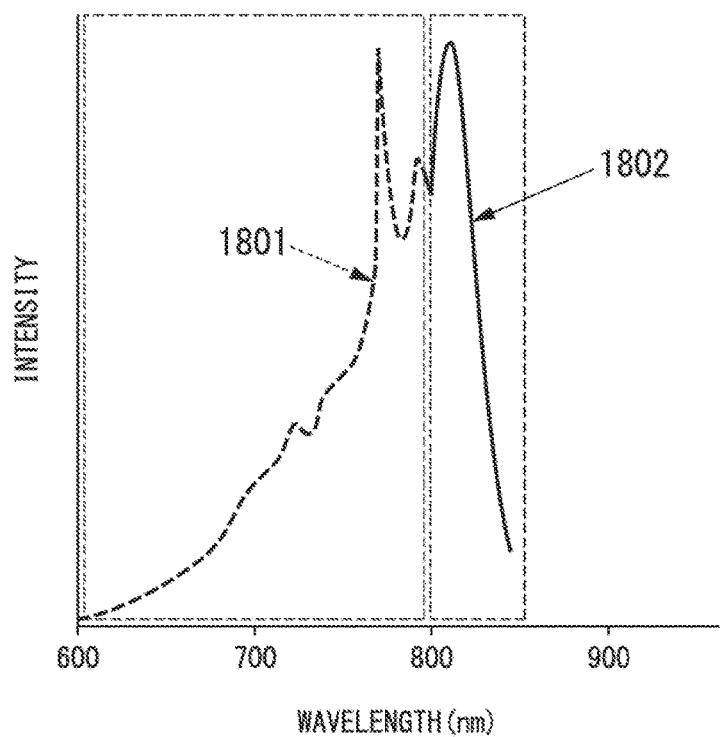
FIG. 18 is a graph which shows characteristics of an excitation wavelength and a fluorescence wavelength of a conventionally known ICG fluorescence substance.
Figure 19:
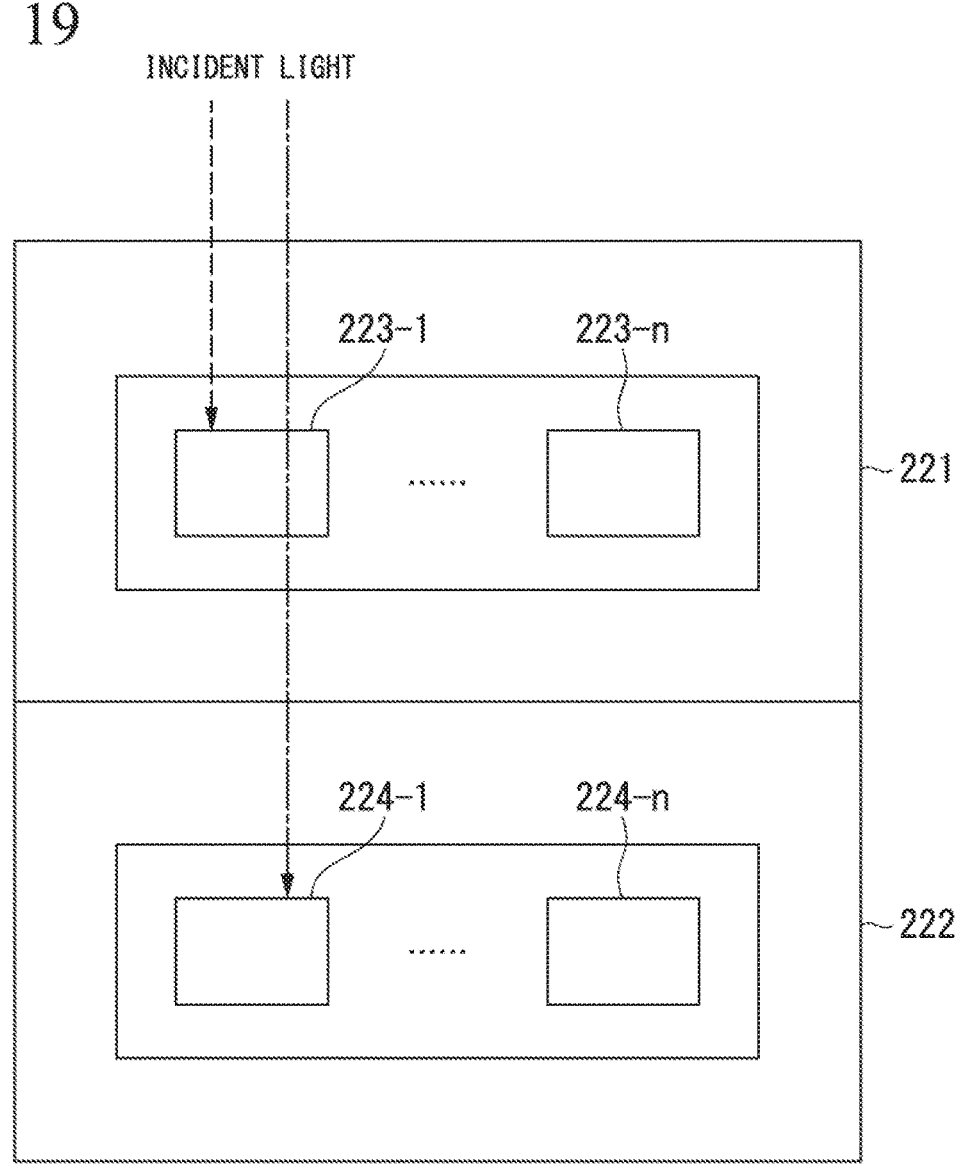
FIG. 19 is a cross-sectional view which shows a conventionally known image pickup element of a hybrid structure in which two layers are stacked and image pickup is performed in a lower layer using light transmitted through an upper layer.
Figure 20:
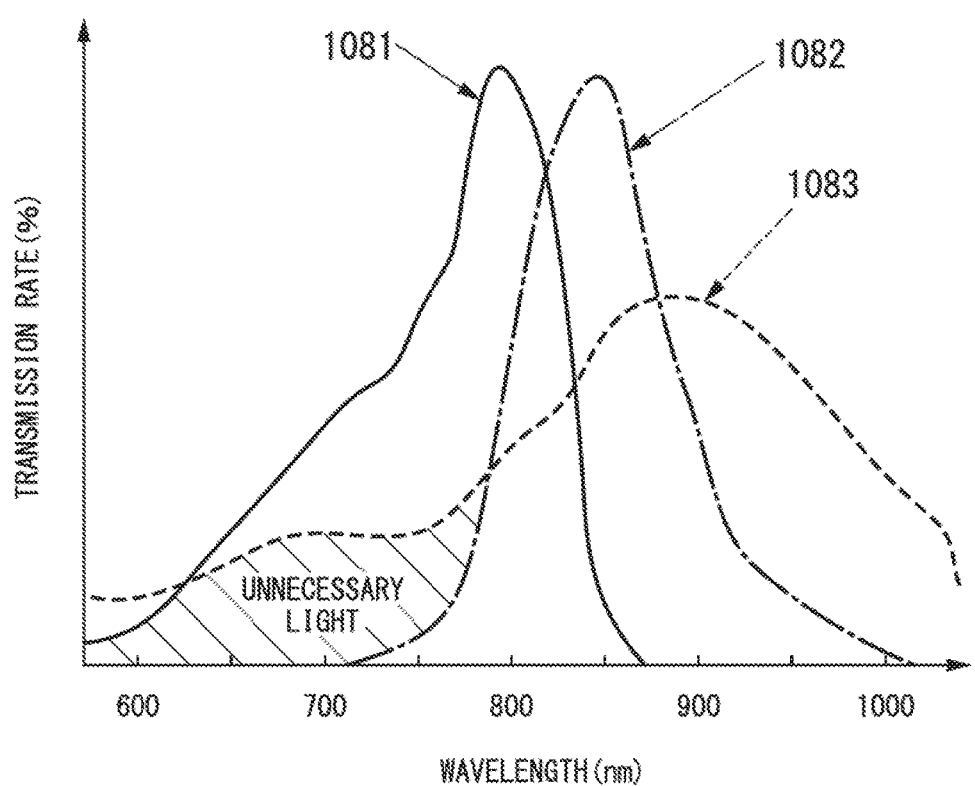
FIG. 20 is a graph which shows conventionally known ICG fluorescence characteristics and characteristics of the stacked image pickup elements.

FIG. 13 is a block diagram which shows a configuration of an image pickup element 1100 in the present embodiment. The image pickup element 1100 includes a light amount adjustment unit 1101. The third signal generated by the first PN junction surfaces 1041-1 to 1041-n is a signal corresponding to an amount of excitation light. For example, since an excitation wavelength of a fluorescence substance is also in the infrared band, an observer cannot visually adjust the amount of excitation light. Therefore, in the embodiment, the light amount adjustment unit 1101 adjusts the amount of light of the light source unit 1004 on the basis of the third signal generated by the first PN junction surface. 1041-1 to 1041-n. As a result, an amount of light radiated to a subject to which the ICG fluorescence substance is administered can be optimized, and thus image quality of fluorescence images can be further improved.

The first embodiment to the seventh embodiment of the present invention have been described in detail above with reference to drawings, but a specific configuration is not limited to these embodiments, and additions, omissions, substitutions, and other changes of the configuration can be performed without departing from the spirit of the present invention. For example, configurations shown in respective embodiments may be combined.

In addition, the present invention is not limited by description provided above, and is limited only by a scope of appended claims.

What is claimed is:

1. An image pickup element comprising:
   a first substrate;
   a second substrate which is stacked on the first substrate;
   first pixels which are disposed in a matrix form on the first substrate, each of the first pixels having a first light-receiving element, the first pixel being irradiated with incident light of a first wavelength band including a visible band and incident light of a second wavelength band having a longer wavelength than the first wavelength band and including a near infrared region, the first pixel generating a first signal corresponding to light of the first wavelength band; and
   second pixels which are disposed in a matrix form on the second substrate and irradiated with light transmitted through the first pixels,
   wherein, in the second pixel, a first P-type layer, an N-type layer, and a second P-type layer are sequentially stacked in an incident direction of incident light,
   the second pixel has:
      a first PN junction surface in which the first P-type layer and the N-type layer are connected and parallel to a light-receiving surface; and
      a second PN junction surface in which the N-type layer and the second P-type layer are connected and positioned deeper than the first PN junction surface and parallel to the light-receiving surface,
   the first P-type layer and the N-type layer of the first PN junction surface are connected at a same potential,
   generation of electric charge at the first PN junction surface with light component having a wavelength included in the first wavelength band among the light transmitted through the first pixels is suppressed, the second PN junction surface detects the light transmitted through the first pixels and the first PN junction surface, and
   the second pixel generates a second signal corresponding to light of the second wavelength band from electric charge obtained by the second PN junction surface.

2. The image pickup element according to claim 1, wherein the first signal is corrected using a third signal generated by the first PN junction surface.

3. The image pickup element according to claim 1, wherein an amount of light incident on the first pixel and the second pixel is controlled using the third signal.

4. An image pickup element comprising:
   a first substrate;
   a second substrate which is stacked on the first substrate;
   first pixels which are disposed in a matrix form on the first substrate, each of the first pixels having a first light-receiving element, the first pixel being irradiated with incident light of a first wavelength band including a visible band and incident light of a second wavelength band having a longer wavelength than the first wavelength band and including a near infrared region, the first pixel generating a first signal corresponding to light of the first wavelength band; and
   second pixels which are disposed in a matrix form on the second substrate and irradiated with light transmitted through the first pixels,
   wherein, in the second pixel, a first P-type layer, an N-type layer, and a second P-type layer are sequentially stacked in an incident direction of incident light,
   the second pixel has:
      a first PN junction surface in which the first P-type layer and the N-type layer are connected and parallel to a light-receiving surface; and
      a second PN junction surface in which the N-type layer and the second P-type layer are connected and positioned deeper than the first PN junction surface and parallel to the light-receiving surface,
   the first P-type layer and the N-type layer of the first PN junction surface are connected at a same potential,
   generation of electric charge at the first PN junction surface with light component having a wavelength included in the first wavelength band among the light transmitted through the first pixels is suppressed, the second PN junction surface detects the light transmitted through the first pixels and the first PN junction surface, and the second pixel generates a second signal corresponding to light of the second wavelength band from electric charge obtained by the second PN junction surface, and
   the first pixel has a third PN junction surface parallel to a light-receiving surface and a fourth PN junction surface positioned deeper than the third PN junction surface and parallel to the light-receiving surface, a P-type layer and an N-type layer of the third PN junction surface are connected at a same potential, and the first pixel generates a fourth signal corresponding to light of the second wavelength band from electric charge obtained by the fourth PN junction surface.

5. An endoscope device which administers a fluorescence substance made of indocyanine green derivative-labeled antibodies to an object to be inspected and performs diagnosis using an endoscope, the endoscope device comprising:
   the image pickup element according to claim 1,
   wherein an optical filter which transmits light of a visible band and a near infrared fluorescence wavelength band of a fluorescence substance and does not transmit an excitation wavelength band component near a fluorescence wavelength band is disposed on a light-receiving surface side of the first pixel, and the first wavelength band includes a visible band and the second wavelength band includes a fluorescence band of the fluorescence substance.

6. An endoscope device which administers a fluorescence substance made of indocyanine green derivative-labeled antibodies to an object to be inspected and performs diagnosis using an endoscope, the endoscope device comprising:

the image pickup element according to claim 4, wherein an optical filter which transmits light of a visible band and a near infrared fluorescence wavelength band of a fluorescence substance and does not transmit an excitation wavelength band component near a fluorescence wavelength band is disposed on a light-receiving surface side of the first pixel, and the first wavelength band includes a visible band and the second wavelength band includes a fluorescence band of the fluorescence substance.

7. The endoscope device according to claim 5, wherein a first image of a visible band is created from the first signal, a second image of a fluorescence wavelength band is created from the second signal, and the first substrate, the second substrate, and the optical filter are disposed at a tip of the endoscope.

8. The endoscope device according to claim 6, wherein a first image of a visible band is created from the first signal, a second image of a fluorescence wavelength band is created from the second signal, and the first substrate, the second substrate, and the optical filter are disposed at a tip of the endoscope.

9. The image pickup element according to claim 1, wherein the first PN junction surface suppresses generation of charges at the first PN junction surface by light component having a wavelength of 600 to 800 nm, and the second PN junction surface detects light component having a wavelength of 800 nm or more among the light transmitted through the first pixels and the first PN junction surface.

10. The image pickup element according to claim 1, wherein charge accumulation time of the first pixels is set to be longer than charge accumulation time of the second pixels, and reading time of the first pixels and the second pixels is set so that the first signal and the second signal have same frame rate.

* * * * *